United States Patent

Mörnberg

[11] 3,975,977
[45] Aug. 24, 1976

[54] MICROTOME

[75] Inventor: Gustav Mörnberg, Stockholm, Sweden

[73] Assignee: Palmstiernas Mekaniska Verkstad AB, Stockholm, Sweden

[22] Filed: Oct. 10, 1974

[21] Appl. No.: 513,901

[30] Foreign Application Priority Data
Oct. 19, 1973  Sweden .................. 7314262

[52] U.S. Cl. .................. 83/707; 83/437; 83/527; 83/915.5; 90/35; 144/178
[51] Int. Cl.² .................. B26D 5/02; B26D 7/06
[58] Field of Search ............ 83/409, 437, 527, 703, 83/707, 713, 714, 715, 716, 915.5, 4; 90/34 R, 35; 144/175, 178, 179

[56] References Cited
UNITED STATES PATENTS

| 199,908 | 2/1878 | Hyatt | 144/175 X |
| 1,454,076 | 5/1923 | Pyle | 90/34 |
| 1,608,404 | 11/1926 | Little | 90/34 |
| 1,615,489 | 1/1927 | Straub | 144/178 |
| 1,797,694 | 3/1931 | Ott | 83/409 X |
| 2,303,213 | 11/1942 | Koss, Jr. | 144/178 |

FOREIGN PATENTS OR APPLICATIONS

| 263,871 | 9/1912 | Germany | 83/915.5 |

Primary Examiner—Othell M. Simpson
Assistant Examiner—Fred A. Silverberg
Attorney, Agent, or Firm—Pollock, Vande Sande & Priddy

[57] ABSTRACT

A microtome for cutting very thin tissue sections from living animals, in situations where extreme accuracy is required. Two rigid, completely closed quadrangular units are arranged for movement relative to one another, one of these units carrying the cutting instrument, the other carrying the object to be cut.

6 Claims, 8 Drawing Figures

MICROTOME

The invention relates to a microtome, comprising a foundation, or housing, a carriage arranged to carry an object, and a knife for cutting thin sections from the object, the knife being vertically positionable for adjusting the thickness of sections and the carriage carrying the object being movable forward and backward on the foundation to bring about a cutting movement.

For many applications in the fields of biology, medicine and pharmacology, very thin sections of tissue from living animals are necessary, e.g., for microscopical examinations. To cut such sections, specialized precision cutting apparatuses called microtomes are employed. The object out of which the tissue section is to be cut is prepared by various techniques, e.g., by embedding the object in paraffin wax for cutting of preparations by so-called paraffin cutting. Since the prepared object must always be softer than the embedding medium, i.e., the paraffin wax, which is rather soft by nature, certain tissues which are rather hard themselves, e.g., teeth, must first be decalcified. Such a decalcification is, however, not only besides time-consuming, but also undesirable in certain cases, for instance in connection with pharmacological examinations as to the localization of medications in various organs. The same applies to preparation methods including, e.g., chemical fixation and stretching of sections on water, since pharmaceuticals are, as a rule, both affected by chemical substances and water-soluble.

A further known process for tissue preparation is the so-called cryostat method. By this method, the object is frozen and sliced to thin preparations by cutting in cold state, contrary to paraffin cutting which is done at room temperature. Cryostat cutting allows cutting of longitudinal sections of whole animal bodies, e.g., animals used in experiments, such as apes, dogs, cats, rats, mice, birds, etc., on different levels through these bodies.

A process for complete body autoradiography, i.e., determination of the concentration of radioactivity marked substances in different organs, is carried out substantially in the manner described below when applied to the cryostat cutting technique:

The substance, the distribution of which in the body is to be examined, is injected in a test animal under anesthesia. The animal is thereafter placed on the object table to a microtome and a metal frame is fastened around the table, so that a box open at the top is formed around the animal. This box is filled with an embedding medium consisting of a semi-liquid gel of carboxymethyl cellulose. The box is thereafter lowered and frozen in hexane cooled to -70°C. by carbon dioxide snow. After a sufficient time in the cooling medium the box is raised and released from the frame. The object then has the form of a frozen block of the embedding medium comprising the test animal and resting on the table. If this block is to be kept for a certain time, it must be stored, for instance in a cooling box at about -20°C. For purposes of cutting, the table is mounted with the frozen block on the microtome. An adhesive tape slip may be fastened on the block before the cutting so as to prevent the thin and fragile sections from falling to pieces, so they can be handled unbroken after the cutting. As the successive sections are taken, they are placed on plastic frames to be freeze dried. Finally, the sections are pressed against a photographic film during the autoradiographic exposure, and the exposure sections and film are separated, whereupon the film is developed.

The cryostat cutting technique gives a frozen object block, that very firmly fixes the object, from which preparation sections are to be taken, so that even the hardest parts of the body, for instance tooth enamel, bones, tendons, etc., can be cut into thin sections without difficulty and without dislocations due to the action of the knife.

Most known microtome cryostats or so-called cryo-microtomes are based on commercially available microtomes for cutting at room temperature of small preparations embedded in paraffin wax. The maximum preparation size thereby is 40 + 40 mm. For cutting of paraffin-embedded preparations, these known microtomes function extremely well, and section thicknesses as small as about 1 $\mu$ are achievable. These microtomes have a carriage carrying the object which is horizontally movable, whereas the object is vertically movable from the carriage. The knife, on the other hand, is fixedly mounted.

When the cryostat technique using such known microtomes is employed for soft preparations embedded in paraffin wax, however, different conditions apply. In this technique one often desires to cut entire test animals and the section area then measures 120 × 40 mm or more, depending on the animal used. Sections thinner than 10 $\mu$ are not obtainable. The sections also get very uneven in thickness along their longitudinal direction and, more precisely, get a wedge shape, thick at one end and thin at the other. A section nominally 10 $\mu$ thick, therefor, may be 20 $\mu$ at its thick end but only 1 - 5 $\mu$ at its thin end. For more exact analyses of the sections, such a shape is most unsatisfactory.

The object of the present invention is to provide a microtome suitable for use with the cryostat technique, and eliminating the disadvantages of the known microtomes when used with this technique. In other words, it permits, on the one hand, preparations of large area sections, and on the other hand very thin sections of uniform thickness.

The embodiments to be described permit cutting of preparations up to a superficial area of 400 × 150 mm and with a section thickness as small as 2 $\mu$. Thanks to the invention, it has become possible to obtain sections below a thickness of 6 $\mu$ thus permitting analyses at the cellular level, whereas the earlier cryostat technique permitted organ analyses only.

Figure 1:
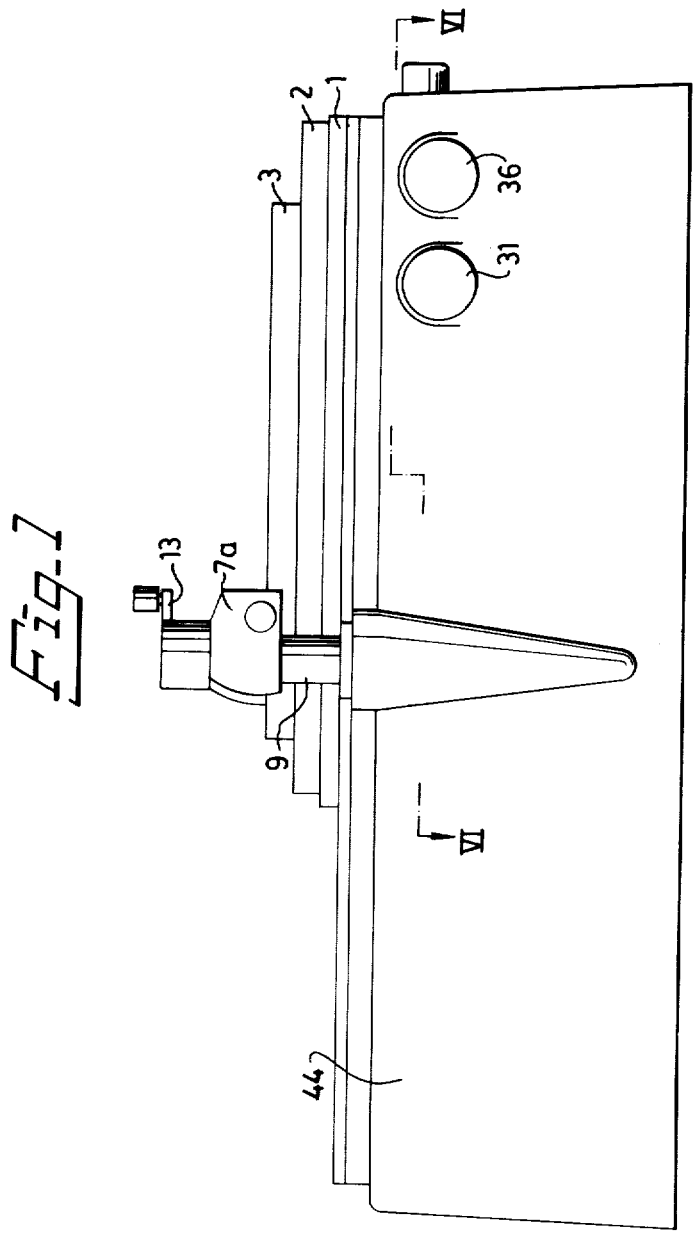
FIG. 1 is a front elevation of a microtome according to the present invention as seen from the front side.
Figure 2:
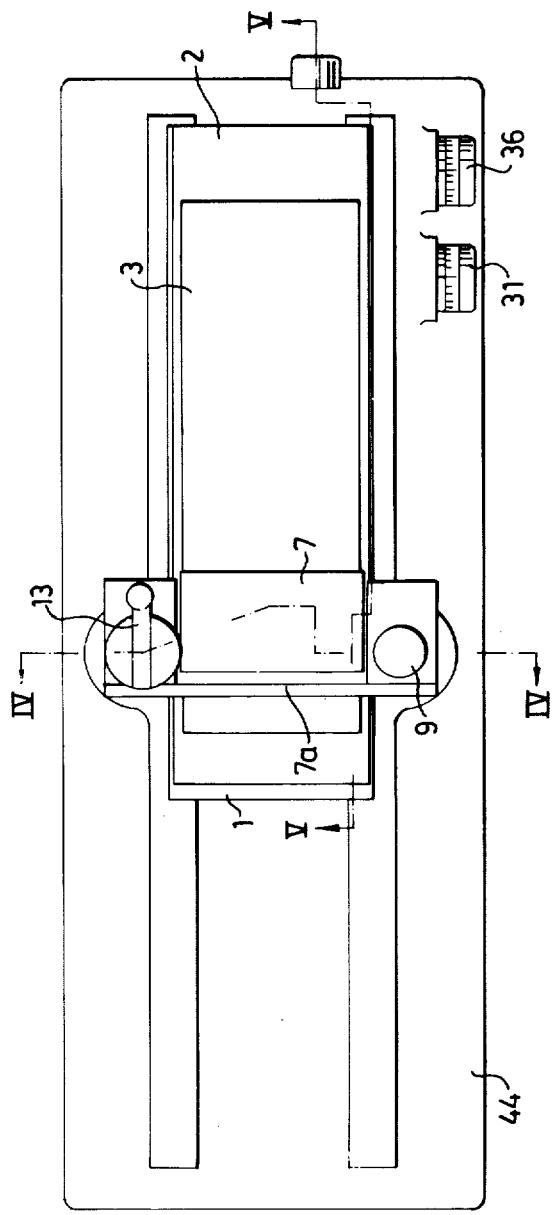
FIG. 2 is a plan view of the microtome.
Figure 3:
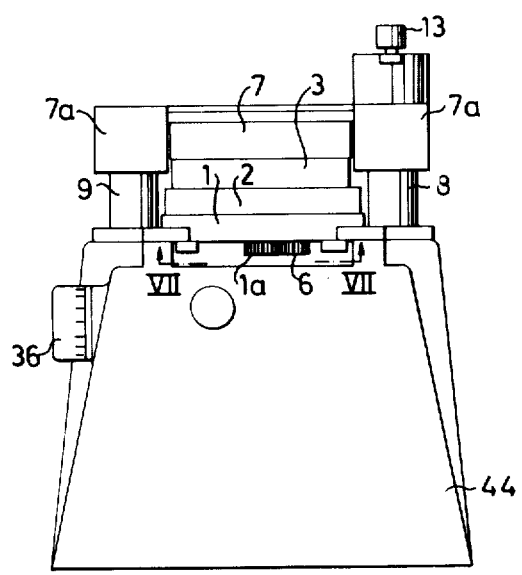
FIG. 3 is an end view as seen from the right hand side of FIG. 1

The microtome shown in FIGS. 1, 2 and 3 is provided with a forward and backward horizontally movable carriage 1, upon which a preparation table 2 can be fastened. A rectangular, frozen object 3, from which a preparation section is to be cut, is placed on the table 2. A knife holding device 7a is attached to two vertical columns 8 and 9. A crank 13 for manual adjustment of the knife holder 7a and thereby also of the knife 7, held by the knife holder, is supported by column 8. The base or housing 44 has two knobs 31 and 36 for small increment feeding, and large increment feeding respectively of the knife 7. The knife 7 can be operated both manually, through crank 13, and automatically, by setting knobs 31 and 36. These knobs are graduated within the range 0 – 200 μ with 10 μ intervals for the knob 36, and within the range 0 – 40 μ with 2 μ intervals for the knob 31, for controlling the automatic vertical downward feeding of knife 7 at each cut during operation of the microtome. In the end view of FIG. 3, besides the parts discussed above, is shown a toothed path 1a attached to the underside of carriage 1 and meshing with a gear wheel 6 for imparting oscillating horizontal movement to the toothed path and thereby to the carriage, as will be explained in detail hereinafter.

Figure 4:
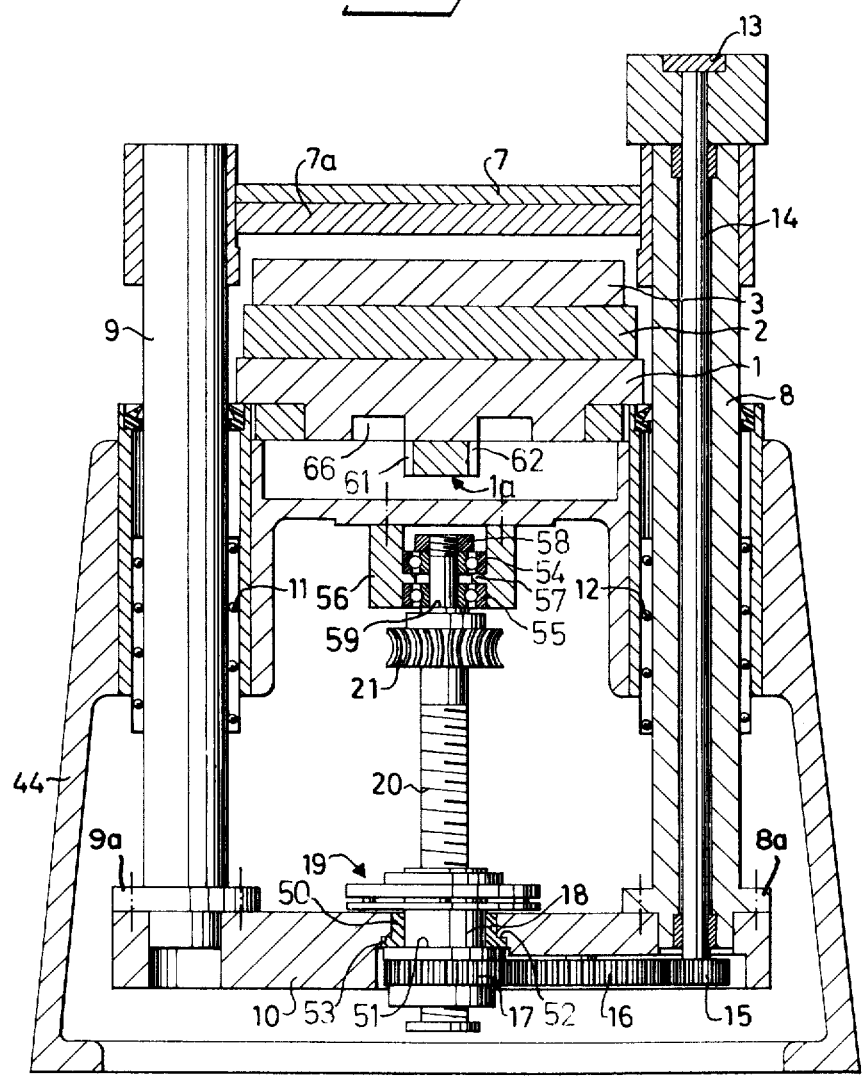
FIG. 4 is a section along the line IV—IV of FIG. 2.

FIG. 4 shows the mechanism for conveying movement to the knife 7 by activating crank 13. The knife holder 7a extends over the space between columns 8 and 9 and is sleeve-like at both ends so as to encircle the respective column on which it is clamped. A bridge 10 is clamped against flanges 8a, 9a of the respective columns 8, 9 by means of screws indicated by dotted lines, thereby to join the lower ends thereof. The rigid unit thus constituted by knife holder 7a, columns 8 and 9 and bridge 10 is vertically movable relative to housing 44 and carriage 1 in ball bearing guides 11 and 12 respectively Crank 13 is connected to a shaft 14 extending centrally through column 8 and carrying in its lower end a gear wheel 15. This gear wheel meshes with an intermediate gear wheel 16, which in turn meshes with a central gear wheel 17, which is integral with a nut 18. Nut 18 is threadably engaged with a vertical screw 20, which at its upper end is rotatably supported by the microtome housing, and whose lower end extends through nut 18 as well as gear wheel 17. Nut 18 is rotatably housed in a bushing 50, which is pressed into bridge 10. A flange 51 of nut 18 bears against bushing 50, which in turn bears through a flange 52 against a shoulder 53 in the hole in bridge 10, wherein bushing 50, nut 18 and gear wheel 17 are located. By this arrangement, the frame-like structure constituted by bridge 10, columns 8 and 9 and knife holder 7a hangs in the screw 20 through nut 18 and bushing 50.

Screw 20 is supported in its upper, unthreaded end in a bearing constituted by two roller bearings 54 and 55 respectively. Bearings 54 and 55 are positioned in a bearing housing 56, which is screwed against a plane, downwardly facing surface of the base or housing 44. Bearing housing 56 has an inwardly directed flange 57 against opposite sides of which the outer rings of bearings 54 and 55 bear by means of the bearings being clamped together between a nut 58 threaded on the end of the screw and a shoulder 59 on the screw 20 which act against the inner ring of the respective bearing.

Secured to screw 20 below the bearing described is a worm wheel 21 meshing with a worm 22 (FIG. 6), which is moved by a mechanism for the automatic feeding of the knife, as will be described below. The worm gear made up of worm wheel 21 and worm 22 is self-braking in respect of the movement of screw 20. Thus, by actuating crank 13, it is possible to raise or lower bridge 10 with knife holder 7a and knife 7 for pre-adjustment of the knife relative to object 3, before the automatic feeding of the knife described below is begun.

The mechanism for the automatic gradual downward feeding of knife 7 is described with reference to FIG. 5 and 6, which show a vertical and a horizontal section, respectively, through the microtome according to the invention. The feeding mechanism imparts movement to the above-mentioned worm 22, which in turn through worm wheel 21, transmits the movement to screw 20. A frictional device 19 fixedly attached to nut 18 holds nut 18 stationary relative to bridge 10, so that the step-by-step rotation of screw 20 results in a lowering of knife 7. As the frictional device 19 does not constitute an essential part of the invention, it will not be described in detail. From the description given above it will be obvious, however, that its function is such, that the nut 18 is allowed to rotate due to actuation of crank 13, whereas it is held stationary during rotation of screw 20.

Worm pinion 22 is actuated by means of a pinion and rack arrangement. In FIG. 5 the carriage 1 is shown near its right end position during the return movement, i.e., to the right. A boss 25 is mounted on the underside of carriage 1 and upon movement to the right of carriage 1 is adapted to actuate the upper ends of two arms 23 and 24 which at their lower ends are pivoted to base 44. A rack 26 is pivoted to arm 23 and adapted to co-operate with a pinion 27. Pinion 27 is adapted to rotate worm 22 meshing with worm wheel 21 by means of a pawl 28 (FIG. 6) and a ratchet wheel 29. A rack 40 is correspondingly pivoted to arm 24 and adapted to co-operate with a pinion 45. Rack 40 meshes with pinion 45 from below (FIG. 5) and is supported by bracket 47. Pinion 45 is adapted to rotate worm 22 by means of a pawl 43, a ratchet wheel 41, a gear wheel 46 and a gear wheel 48 mounted on the same shaft as worm 22.

Arm 23 is forced to the left by a spring 30. A corresponding spring forces arm 24 to the left. Knob 31 is connected to a pinion 33 meshing with a rack 32, and knob 36 is connected to a pinion 37 meshing with a rack 42. Rack 32 has a pin 34 which prevents rack 26 from return movement further than is allowed by a pin 34 on rack 26. Correspondingly, rack 42 has a pin 39 which prevents rack 40 from returning further than is allowed by a pin 38 on rack 40.

Figure 5:
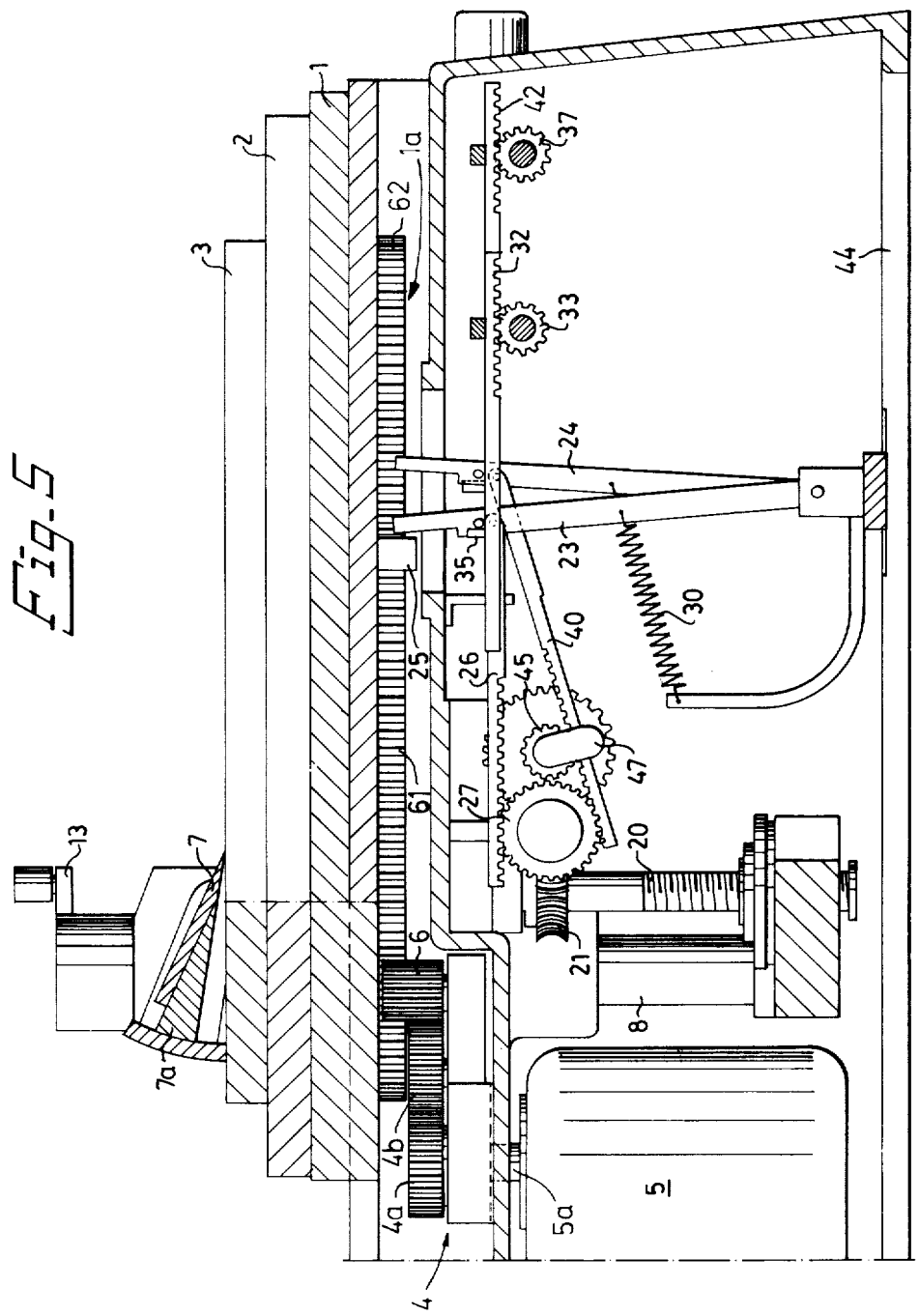
FIG. 5 is a section along the line V—V of FIG. 2.
Figure 6:
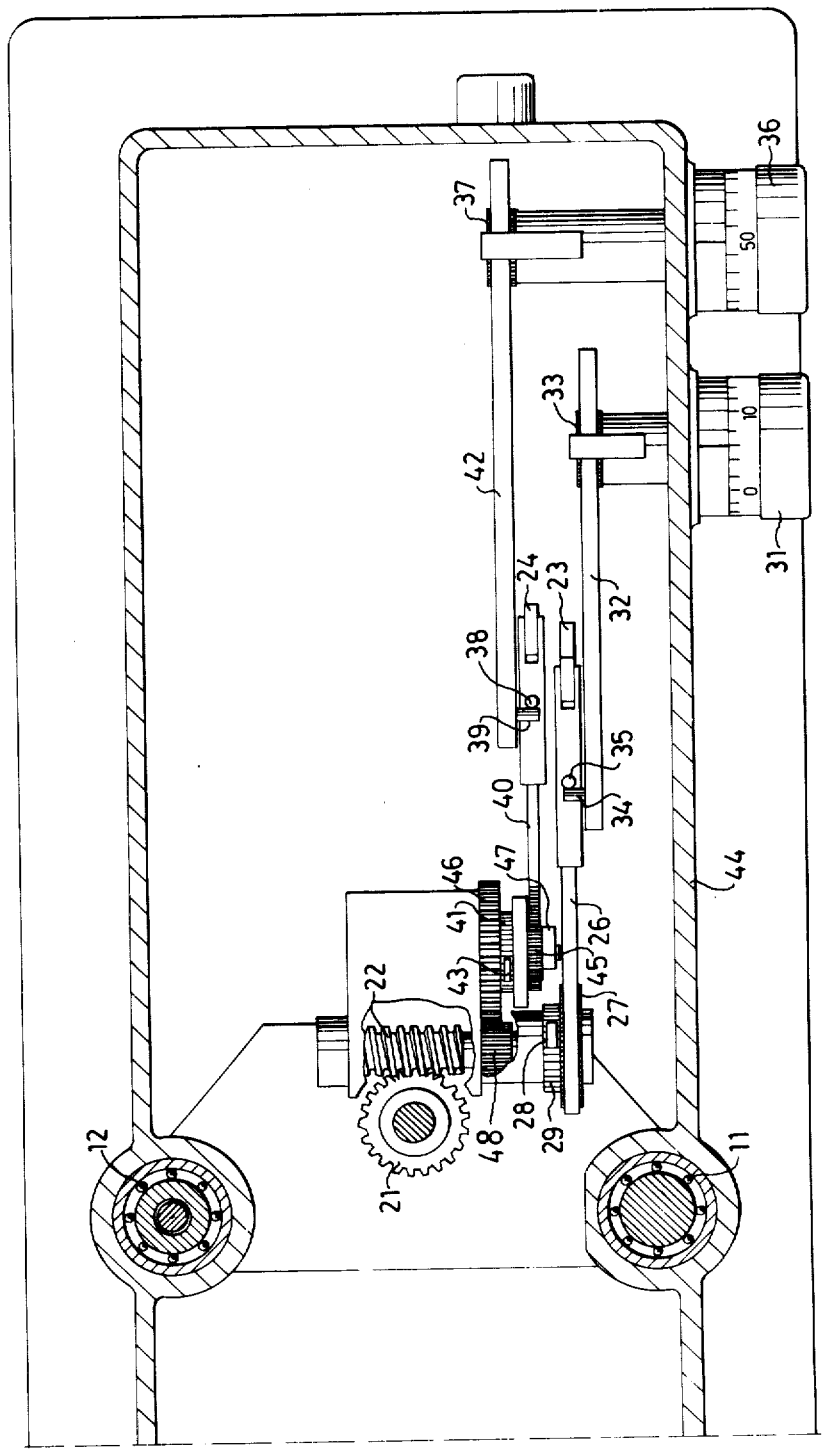
FIG. 6 is a section along the line VI—VI of FIG. 1.
Figure 7:
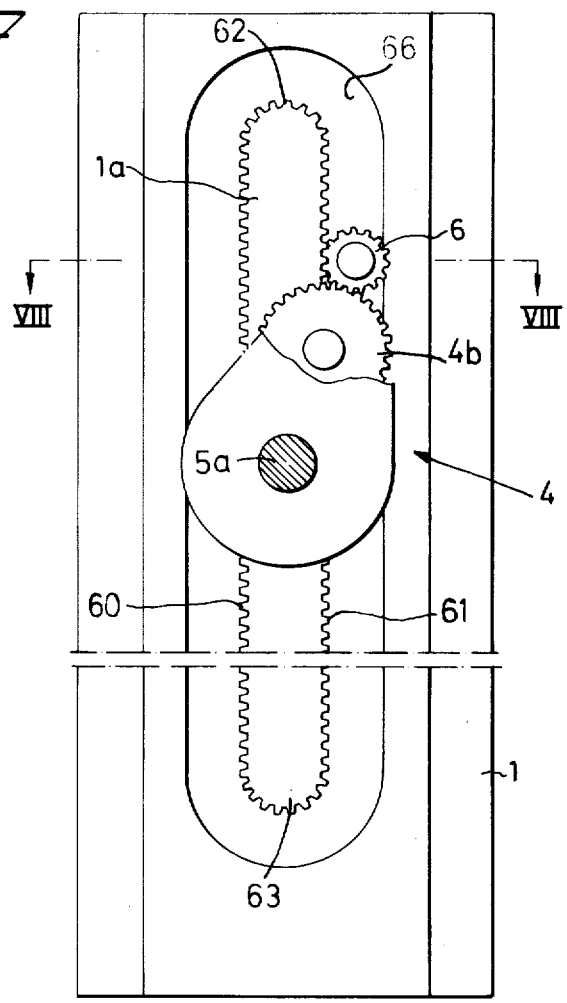
FIG. 7 is a sectional view from underneath taken along the line VII—VII of FIG. 3.
Figure 8:
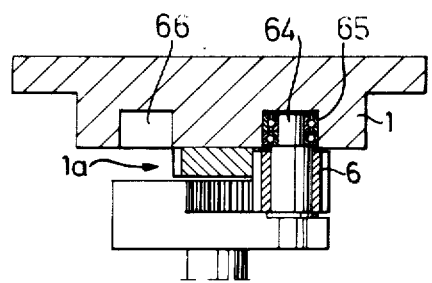
FIG. 8 is a section taken along the line VIII—VIII of FIG. 7.

FIGS. 5, 7 and 8 show the mechanism for imparting to-and-fro movement to the carriage 1. This mechanism comprises a motor 5 carrying a drive 4 swingable around the driving shaft 5a of the motor, the drive 4 including a gear wheel 4a driven by the motor, an intermediate gear wheel 4b meshing therewith and finally a pinion 6 meshing with the last mentioned gear wheel. Pinion 6 also meshes with a toothed path 1a, which includes two parallel racks 60, 61 with outwardly facing teeth and two semi-circular toothed parts 62 and 63 joining the ends of the racks. Pinion 6 is provided with an upwardly extending shaft end 64 (FIG. 8) which carries a roller bearing 65 adapted to roll in a groove 66 milled in carriage 1 to follow the toothed path, whereby the pinion is guided continuously towards the toothed path 1a, so that the pinion will move around the path and thereby give the carriage its intended oscillating movement.

The microtome according to the present invention functions in the following manner:

The object 3 is placed on the preparation table 2 and the knife 7, which is to cut thin sections from object 3, is manually placed into abutting relationship with the object by actuation of crank 13 which, via shaft 14, gear wheels 15, 16, 17, nut 18 and screw 20, imparts the desired vertical movement to the frame-like unit 7a, 8, 9, 10 guided in ball bearing guides 11, 12 and including the knife 7.

Subsequently the microtome is set for automatic downward feeding of the knife 7 a predetermined distance, corresponding to the desired thickness of the section to be taken from object 3 upon each movement to the right (as seen in FIG. 5) of carriage 1.

The feeding step of knife is set through knobs 36 or 31 for large increment feeding, or small increment feeding respectively. Examples of the graduation of the knobs have been given above. The function in connection with setting of knob 31 will now be described.

It is assumed that the carriage 1 moves towards its end position to the right of FIG. 5, i.e., performs a return movement. The boss 25 under the carriage then moves arms 23, 24 to the right. By the movement of arm 23, the rack 26 pivoted thereto due to its meshing with pinion 27 will rotate same a certain distance clockwise. This movement is transferred by pawl 28 to the ratchet wheel 29, the worm 22 and the worm wheel 21. As the carriage has reached its end position and starts moving to the left, arm 23 is also forced to the left by spring 30. Thereby pinion 27 is also rotated to the left and the pawl 28 passes over a certain number of teeth of ratchet wheel 29. This number of teeth corresponds to the magnitude of downward feeding for the following cutting stroke of carriage 1.

The number of teeth corresponding to the feeding increment of knife 7 relative to object 3 is determined by the setting of knob 31. With this knob the return movement of arm 23 under the influence of spring 30 can be limited to a distance corresponding to the desired feeding increment. This is carried out by rack 32 and pinion 33 attached to knob 31. Pin 34 on rack 32 thereby prevents rack 26 from returning further than to abutment of pin 34 against pin 35 on the last mentioned rack. Thus, by means of knob 31, the number of teeth caught by pawl 28 on ratchet wheel 29 for every return stroke of carriage 1 is controlled.

The mechanism between the large increment feeding knob 36 and ratchet wheel 41, which mechanism includes pinion 37, rack 42 with pin 39, rack 40 with pin 38, pinion 45 and pawl 43, functions in the same manner as the one just described, the only difference being that this last described mechanism relative to the former one gives a feed ratio 1:5 achieved by gear wheels 46 and 48.

In a recently developed cryo-microtome incorporating a microtome according to the invention, the microtome is housed in a refrigerator box or cryostat and is electronically controlled from outside the box. The microtome carriage is driven back and forth by a speed-controlled, d.c. electric motor. Potentiometers sense the positions of the carriage and the knife, and give information thereon to the control logic. In this embodiment the knife is driven up or down by means of a stepping motor actuating worm wheel 21. The control logic also receives information from different kinds of controls such as motor controls, speed control, stroke length control, stroke counter, knife feeding control and temperature sensor, in order to perform a completely automatic operation of the cryo-microtome.

I claim:
1. A microtome, comprising:
  a. a base having a unitary, rigid structure;
  b. a carriage for carrying an object, the carriage being mounted on the base for reciprocating horizontal movement;
  c. a completely closed, rectangular frame-like unit vertically movable relative to the base, comprising
     i. a knife holder having two ends;
     ii. two vertical columns having their upper ends rigidly secured to the respective ends of the knife holder; and
     iii. a horizontal bridge rigidly connecting the lower ends of the vertical columns below the carriage;
  d. a knife for cutting sections from the object, the knife being mounted substantially horizontally in the knife holder for vertical movement with the frame-like unit for adjusting the thickness of the sections to be cut;
  e. means surrounding the columns over a substantial part of their length provided in opposed walls of the base, for slidably guiding axial movement of the columns;
  f. centrally disposed crew means rotatably depending from the upper wall of the base below the carriage;
  g. a nut centrally disposed in the horizontal bridge cooperating with the screw means;
  h. the frame-like unit hanging from the screw means and being vertically adjustable by the screw means.
2. a microtome according to claim 1, wherein the base has a box-like structure of quadrangular cross-section.
3. a microtome according to claim 1, wherein the screw means comprises a single screw.
4. a microtome according to claim 1, wherein the screw means is actuatable from the exterior of the base.
5. a microtome according to claim 1, further including a step feeding device, a worm connected to the step feeding device, a worm wheel actuated by the worm in response to movement of the carriage, the worm wheel imparting its rotational movement to the screw.
6. A microtome according to claim 5, wherein the rotational movement is imparted to the screw as the carriage is substantially in its end position after a return stroke.

* * * * *